(12) United States Patent
Kobayashi

(10) Patent No.: US 11,823,441 B2
(45) Date of Patent: Nov. 21, 2023

(54) MACHINE LEARNING APPARATUS, MACHINE LEARNING METHOD, AND NON-TRANSITORY COMPUTER-READABLE STORAGE MEDIUM

(71) Applicant: CANON KABUSHIKI KAISHA, Tokyo (JP)

(72) Inventor: Tsuyoshi Kobayashi, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/675,071

(22) Filed: Feb. 18, 2022

(65) Prior Publication Data
US 2022/0172461 A1    Jun. 2, 2022

Related U.S. Application Data

(63) Continuation of application No. PCT/JP2020/028193, filed on Jul. 21, 2020.

(30) Foreign Application Priority Data

Aug. 30, 2019    (JP) ................................. 2019-158927

(51) Int. Cl.
*G06V 10/00*    (2022.01)
*G06V 10/774*    (2022.01)
(Continued)

(52) U.S. Cl.
CPC ........ *G06V 10/7747* (2022.01); *G06T 3/0006* (2013.01); *G06V 10/22* (2022.01); *G06V 10/82* (2022.01)

(58) Field of Classification Search
CPC ........ G06N 20/00; G06N 3/08; G06N 3/0454; G06V 10/7747; G06V 10/82; G06V 10/22;
(Continued)

(56) References Cited

U.S. PATENT DOCUMENTS 9,418,417 B2    8/2016    Kobayashi
9,813,647 B2    11/2017    Kobayashi
(Continued)

FOREIGN PATENT DOCUMENTS

JP    H04-261649 A    9/1992
JP    2017-185007 A    10/2017
(Continued)

OTHER PUBLICATIONS

International Search Report issued by the Japan Patent Office dated Oct. 20, 2020 in corresponding International Application No. PCT/JP2020/028193, with English translation.
(Continued)

*Primary Examiner* — Amir Alavi
(74) *Attorney, Agent, or Firm* — Carter, DeLuca & Farrell LLP

(57) ABSTRACT

A machine learning apparatus for extracting a region from an input image, comprises: an inference unit configured to output the region by inference processing for the input image; and an augmentation unit configured to, in learning when learning of the inference unit is performed based on training data, perform data augmentation by increasing the number of input images constituting the training data, wherein the augmentation unit performs the data augmentation such that a region where image information held by the input image is defective is not included.

29 Claims, 6 Drawing Sheets

(51) Int. Cl.
  *G06V 10/82* (2022.01)
  *G06V 10/22* (2022.01)
  *G06T 3/00* (2006.01)
(58) Field of Classification Search
  CPC ....... G06V 10/774; G06T 7/11; G06T 3/0006; G06T 2207/10116; G06T 2207/20081; G06T 2207/20084
  See application file for complete search history.

(56) References Cited

U.S. PATENT DOCUMENTS

| | | | |
|---|---|---|---|
| 9,979,911 B2 | 5/2018 | Kobayashi | |
| 10,872,409 B2* | 12/2020 | Schafer | G06T 7/155 |
| 10,997,716 B2* | 5/2021 | Zaharchuk | G06T 3/60 |
| 11,276,490 B2* | 3/2022 | Hong | G06N 3/08 |
| 11,321,610 B2* | 5/2022 | Srinivasaraghavan | G06F 16/78 |
| 11,327,497 B2* | 5/2022 | Gong | G06N 3/08 |
| 11,340,700 B2* | 5/2022 | Park | G06T 11/00 |
| 11,461,537 B2* | 10/2022 | Lundgaard | G06N 3/04 |
| 11,599,788 B2* | 3/2023 | Girard | G06F 17/18 |
| 2018/0107928 A1 | 4/2018 | Zhang | |
| 2018/0190377 A1* | 7/2018 | Schneemann | A61B 5/7485 |
| 2019/0065884 A1 | 2/2019 | Li | |
| 2020/0019760 A1* | 1/2020 | Ma | G06V 40/16 |
| 2020/0057907 A1 | 2/2020 | Kobayashi | |
| 2022/0058423 A1 | 2/2022 | Kobayashi | |
| 2022/0172461 A1* | 6/2022 | Kobayashi | G06V 10/7747 |
| 2022/0196463 A1* | 6/2022 | Han | H04B 10/2537 |

FOREIGN PATENT DOCUMENTS

| | | |
|---|---|---|
| JP | 2019-076699 A | 5/2019 |
| JP | 2020-014799 A | 1/2020 |

OTHER PUBLICATIONS

Amano Toshiyuki et al., "Image Interpolation Using BPLP Method on the Eigenspace" Proceedings of IEICE, D-11 (Mar. 2002) pp. 457-465, vol. J85-D-II, No. 3, with English translation.

Do, Nt et al., "Knee Bone Tumor Segmentation from radiographs using Seg / Unet with Dice Loss" Research Gate (Feb. 2019) pp. 1-6.

Stack Overflow, "Keras ImageDataGenerator with center crop for rotation and translation shift" (May 2019) https://stackoverflow.com/questions/56254393/keras-imagedatagenerator-with-center-crop-for-rotation-and-translation-shift, pp. 1-3.

Jang, Y. et al., "Estimating Compressive Strength of Concrete Using Deep Convolutional Neural Networks with Digital Microscope Images" Research Gate (May 2019) pp. 1-12.

Notice of Reasons for Refusal issued by the Japanese Patent Office dated Oct. 6, 2023 in corresponding JP Patent Application No. 2019-158927, with English translation.

* cited by examiner

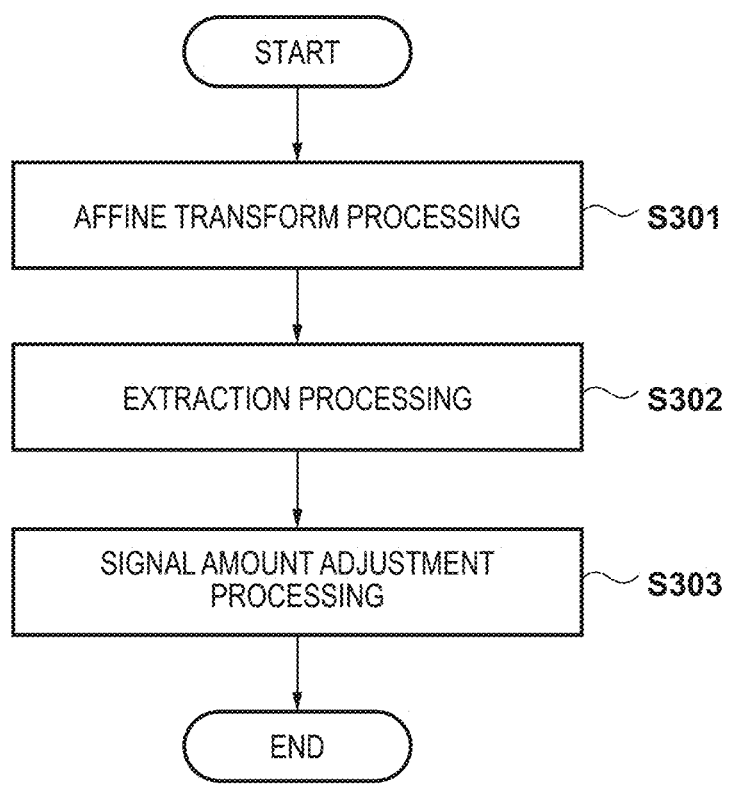

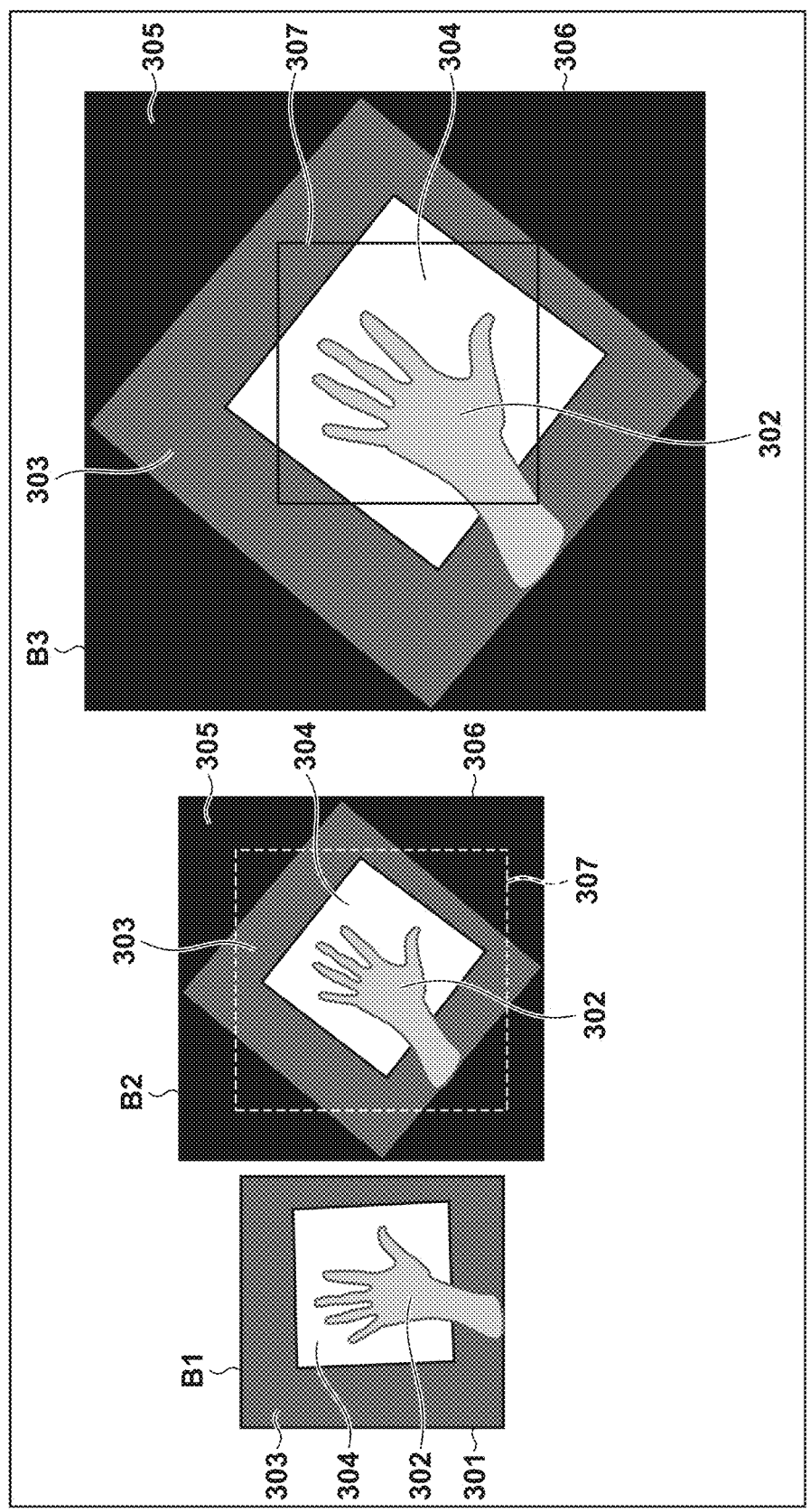

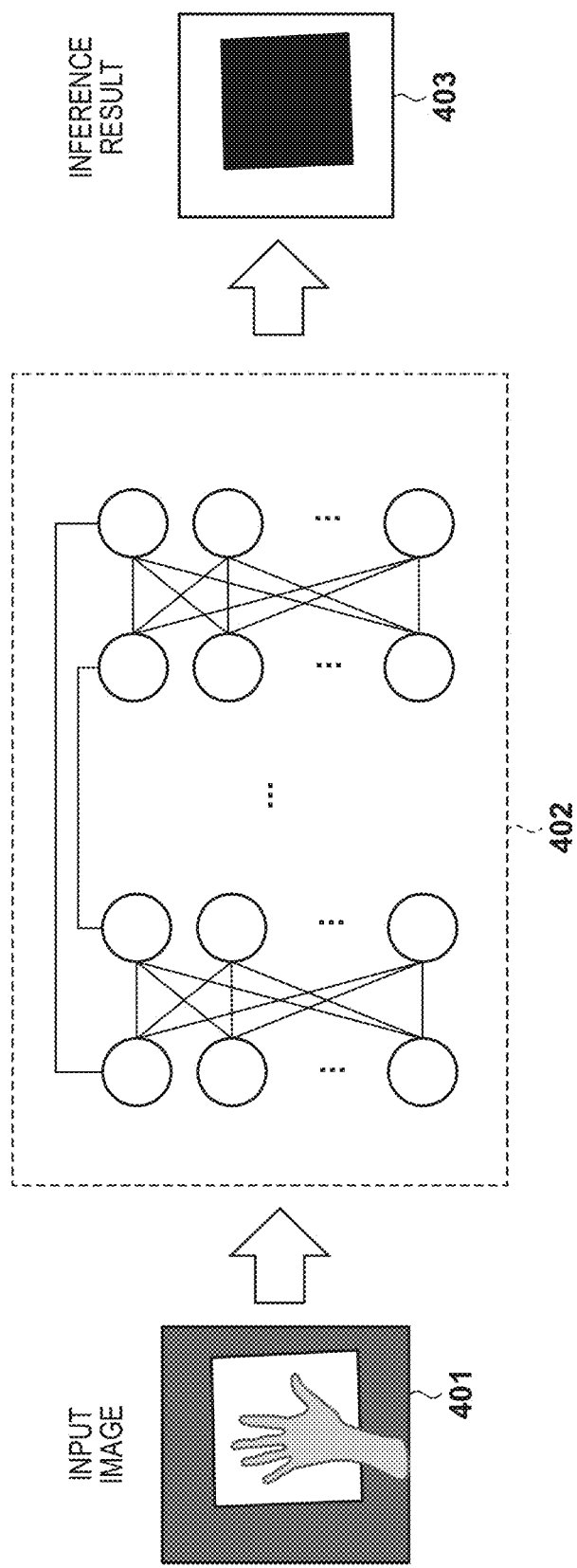

MACHINE LEARNING APPARATUS, MACHINE LEARNING METHOD, AND NON-TRANSITORY COMPUTER-READABLE STORAGE MEDIUM

CROSS-REFERENCE TO RELATED APPLICATIONS

This application is a Continuation of International Patent Application No. PCT/JP2020/028193, filed Jul. 21, 2020, which claims the benefit of Japanese Patent Application No. 2019-158927, filed Aug. 30, 2019, both of which are hereby incorporated by reference herein in their entirety.

BACKGROUND OF THE INVENTION

Field of the Invention

The present invention relates to a machine learning apparatus, a machine learning method, and a non-transitory computer-readable storage medium storing a program and, more particularly, to a machine learning technique capable of appropriately augmenting training data at the time of learning.

Background Art

In recent years, a technique of performing object recognition on an image using machine learning and detecting the position of a target has become popular. In particular, a configuration for performing supervised learning using a convolutional neural network (to be referred to as a "CNN" hereinafter) has been deployed in a lot of fields because of its high performance.

One of the application fields is region extraction processing in a medical image. In a medical radiation imaging apparatus, to suppress the influence of radiation to regions other than a region of interest (to be referred to as an "irradiation field" hereinafter) necessary for diagnosis, in general, the irradiation field is narrowed using a collimator, thereby preventing radiation irradiation to regions other than the irradiation field. To perform image processing for an irradiation field, a technique of correctly extracting an irradiation field in an image is important, and, for example, PTL 1 proposes various kinds of techniques using machine learning.

As a characteristic feature of image processing using machine learning, the quality and amount of training data are directly associated with the performance. It is therefore preferable to use a large amount of training data for learning. However, for images such as medical images whose availability is not necessarily high, it is often impossible to ensure sufficient training data.

For this reason, there has been proposed a data augmentation technique for increasing variations of images by artificially deforming held training data. For example, PTL 2 proposes a technique of augmenting data by rotating an image.

CITATION LIST

Patent Literature

PTL 1: Japanese Patent Laid-Open No. 04-261649
PTL 2: Japanese Patent Laid-Open No. 2017-185007

The technique of PTL 2 performs data augmentation by rotating an image to a plurality of angles. If an image is simply rotated, the image after the rotation may include a region where image information (image signal) is defective. In general, an arbitrary value such as zero is substituted into the region where image information is defective.

Consider the case of the above-described medical radiation imaging apparatus. In regions other than the irradiation field, since radiation is shielded by the collimator, image information exists only in a small amount or is almost zero. That is, when recognizing the irradiation field, that the amount of image information derived from the input image is small and is one of the features to be learned. Hence, if a region where the image information is uniformly set to an arbitrary value such as zero is newly created by data augmentation, it may be impossible to do learning, and the accuracy may be lowered by data augmentation.

The present invention has been made in consideration of the above-described problem, and provides a machine learning technique capable of more accurately extracting a region by performing appropriate data augmentation for training data used in learning.

SUMMARY OF THE INVENTION

According to one aspect of the present invention, there is provided a machine learning apparatus for extracting a region from an input image, comprising: an inference unit configured to output the region by inference processing for the input image; and an augmentation unit configured to, in learning when learning of the inference unit is performed based on training data, perform data augmentation by increasing the number of input images constituting the training data, wherein the augmentation unit performs the data augmentation such that a region where image information held by the input image is defective is not included.

According to another aspect of the present invention, there is provided a machine learning method by a machine learning apparatus including inference unit configured to output a region by inference processing for an input image and configured to extract the region from the input image, comprising performing, in learning when learning of the inference unit is performed based on training data, data augmentation by increasing the number of input images constituting the training data, wherein the data augmentation is performed such that a region where image information held by the input image is defective is not included.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 3A is a flowchart showing the procedure of processing of a data augmentation unit;

FIG. 3B is a view schematically showing image examples in data augmentation processing;

FIG. 4 is a schematic view showing the concept of inference in an inference unit.

DESCRIPTION OF THE EMBODIMENTS

Figure 1:
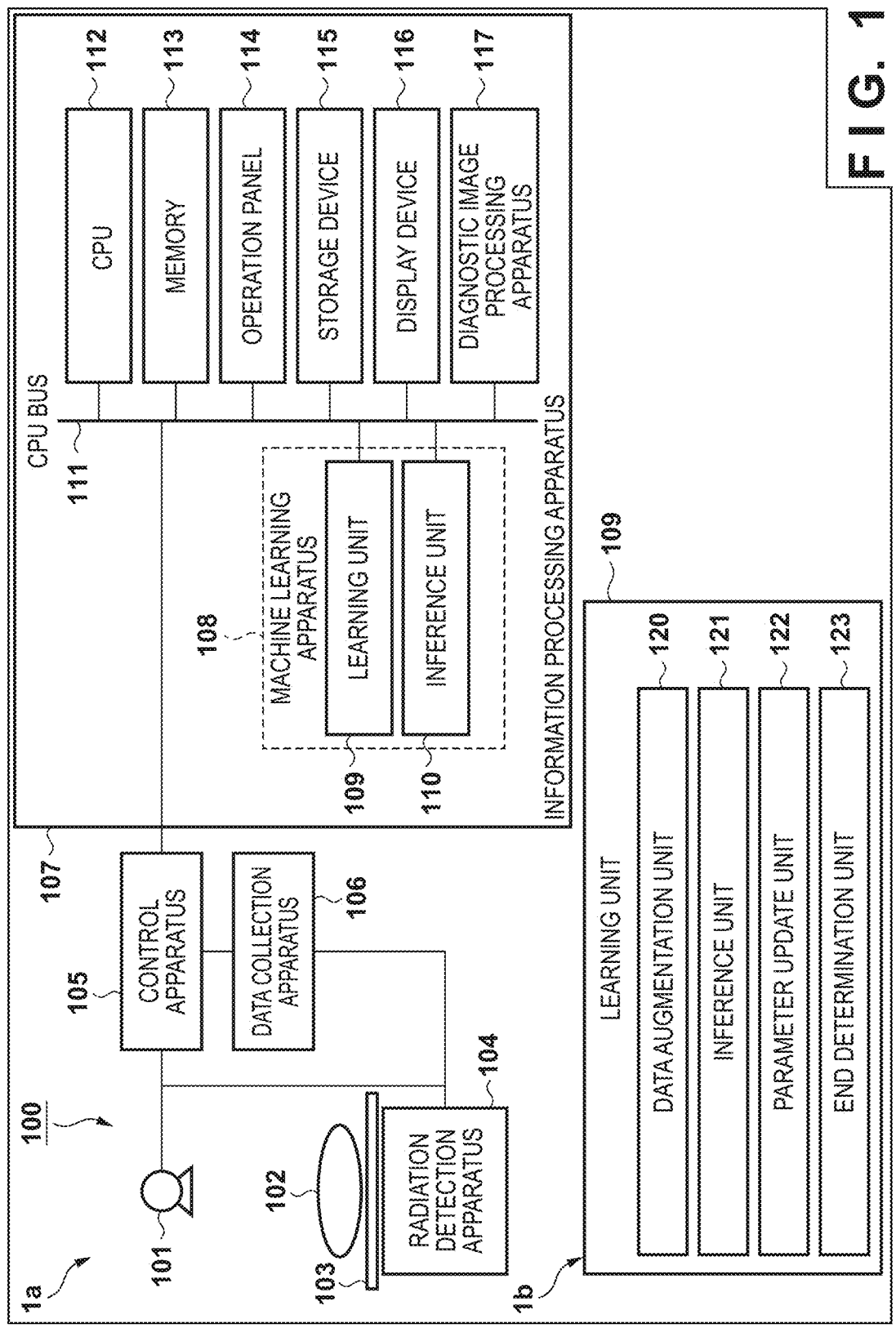
FIG. 1 shows a block diagram 1a showing an example of the basic configuration of a radiation imaging system including a machine learning apparatus according to the embodiment, and a block diagram 1b showing an example of the configuration of a learning unit.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

In FIG. 1, 1a is a block diagram showing an example of the basic configuration of a radiation imaging system including a machine learning apparatus according to the embodiment. In addition, 1b in FIG. 1 is a block diagram showing an example of the configuration of a learning unit.

A radiation imaging system 100 includes a radiation generating apparatus 101 that generates radiation, a bed 103 on which an object 102 is arranged, a radiation detection apparatus 104 that detects the radiation and outputs image data according to the radiation that has passed through the object 102, a control apparatus 105 that controls the radiation generating timing and the radiation generating conditions of the radiation generating apparatus 101, a data collection apparatus 106 that collects various kinds of digital data, and an information processing apparatus 107 that controls image processing or the entire apparatus in accordance with a user instruction. Note that the configuration of the radiation imaging system 100 is sometimes called a radiation imaging apparatus.

The information processing apparatus 107 includes a machine learning apparatus 108 including a learning unit 109 and an inference unit 110, a CPU 112, a memory 113, an operation panel 114, a storage device 115, a display device 116, and a diagnostic image processing apparatus 117. These are electrically connected via a CPU bus 111.

The memory 113 stores various kinds of data necessary in processing of the CPU 112, and also includes a work memory for the CPU 112. The CPU 112 is configured to, using the memory 113, control the operation of the entire apparatus in accordance with a user instruction input to the operation panel 114.

In the embodiment of the present invention, radiation is not limited to X-rays to be generally used and includes α-rays, β-rays, γ-rays, and the like, which are beams formed by particles (including photons) emitted upon radioactive decay, and beams (for example, particle rays and cosmic rays) with equal or higher energy.

In accordance with a user instruction via the operation panel 114, the radiation imaging system 100 starts the imaging sequence of the object 102. The radiation generating apparatus 101 generates radiation under predetermined conditions, and the radiation detection apparatus 104 is irradiated with the radiation that has passed through the object 102. Here, the control apparatus 105 controls the radiation generating apparatus 101 based on radiation generating conditions such as a voltage, a current, and an irradiation time, and causes the radiation generating apparatus 101 to generate radiation under the predetermined conditions.

The radiation detection apparatus 104 detects the radiation that has passed through the object 102, converts the detected radiation into an electrical signal, and outputs image data according to the radiation. The image data output from the radiation detection apparatus 104 is collected as digital image data by the data collection apparatus 106. The data collection apparatus 106 transfers the image data collected from the radiation detection apparatus 104 to the information processing apparatus 107. In the information processing apparatus 107, the image data is transferred to the memory 113 via the CPU bus 111 under the control of the CPU 112.

In the radiation imaging system 100, the machine learning apparatus 108 performs region extraction processing for the image data stored in the memory 113, and extracts a region from the input image. Here, the input image is the image captured using the radiation imaging system 100, and the region is the irradiation field irradiated with radiation by the radiation imaging system 100. As the region extraction processing, the machine learning apparatus 108 can perform, for example, irradiation field recognition processing of extracting the irradiation field in the image captured by radiography. Here, the irradiation field recognition processing is processing of classifying a collimator region and an irradiation field, as will be described later. In the following explanation, an example in which the machine learning apparatus 108 performs irradiation field recognition processing as region extraction processing will be described.

The machine learning apparatus 108 is configured to perform region extraction processing using machine learning, and the machine learning apparatus 108 includes the learning unit 109 and the inference unit 110. Also, as shown in 1b of FIG. 1, the learning unit 109 includes, as functional components, a data augmentation unit 120, an inference unit 121, a parameter updating unit 122, and an end determination unit 123. Here, the inference unit 121 is an inference unit halfway through learning. When learning ends, the inference unit 110 is set in the machine learning apparatus 108 as inference unit after learning.

As the processing of the machine learning apparatus 108, for example, a region is extracted from an input image based on supervised learning using a convolutional neural network (CNN). In the machine learning apparatus 108, when performing region extraction processing, the learning unit 109 performs supervised learning using a plurality of training data prepared in advance, and decides parameters of the CNN. When performing region extraction processing, the inference unit 110 performs region extraction processing by applying the CNN having the parameters decided by the learning unit 109, and transfers the region extraction result to the memory 113.

The region extraction result and the image data are transferred to the diagnostic image processing apparatus 117. The diagnostic image processing apparatus 117 applies diagnostic image processing such as gradation processing, emphasis processing, and noise reduction processing to the image data, and creates an image suitable for diagnosis. The result is stored in the storage device 115 and displayed on the display device 116.

Figure 2:
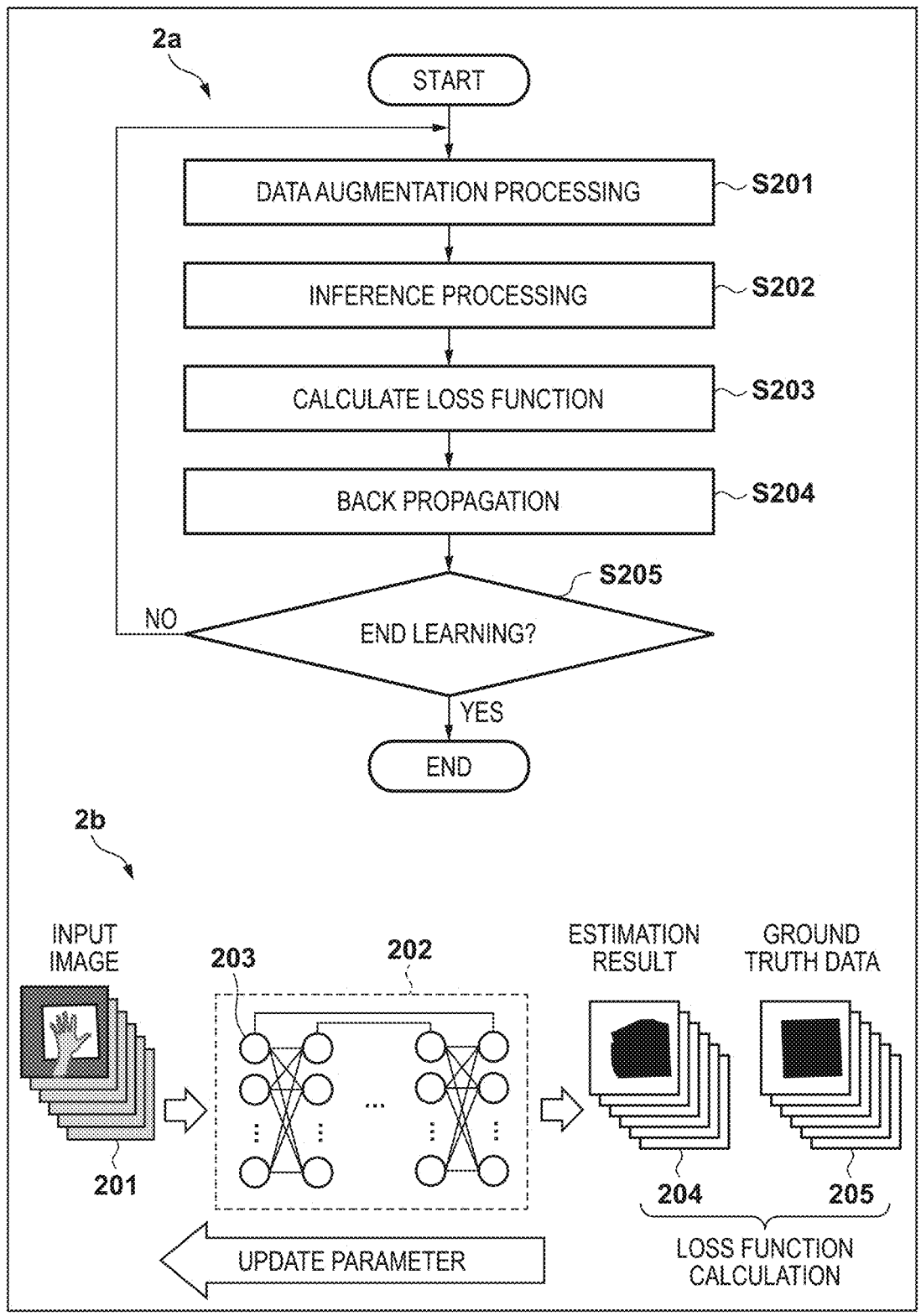
FIG. 2 shows a flowchart 2a showing the procedure of processing of the learning unit, and a view 2b schematically showing the concept of learning of the learning unit.

As for the processing of the learning unit 109 in the machine learning apparatus 108, a case in which a convolutional neural network (CNN) is used will be described as an example with reference to FIG. 2. In FIG. 2, 2a is a flowchart showing the procedure of processing of the learning unit 109, and 2b is a view schematically showing the concept of learning of the learning unit 109.

Learning is performed based on training data. Training data is formed by a set of an input image 201 and ground truth data 205 corresponding to the input image 201 and representing an extraction region. As the ground truth data 205, for example, a labeling image formed by labeling, using an arbitrary value, a predetermined region (extraction region) in the input image can be used. Also, as the ground truth data 205, for example, coordinate data representing the extraction region in the input image by coordinates can be used. Alternatively, as the ground truth data 205, for example, data that specifies the boundary of the extraction region in the input image by a line or a curve can be used. In irradiation field recognition processing, as the ground truth data 205, for example, a binary labeling image in which an irradiation field in the input image 201 is set to 1, and a collimator region is set to 0 can be used.

In step S201, the data augmentation unit 120 applies data augmentation processing to training data. Details of the data augmentation processing will be described later.

In step S202, the inference unit 121 performs, for the input image 201, inference processing using the parameters of the convolutional neural network (CNN) 202 halfway through learning, and outputs an inference result 204. The inference unit 121 outputs a region by inference processing for the input image. Here, the CNN 202 has a structure in which a number of processing units 203 are connected arbitrarily. As the processing unit 203, for example, a convolutional operation, normalization processing, and processing by an activation function such as ReLU or Sigmoid are included, and a parameter group configured to describe the processing contents is provided. In these, sets for performing processes in order, for example, convolutional operation→normalization→activation function, are connected in three to several hundred layers, and various structures can be taken.

In step S203, the parameter updating unit 122 calculates a loss function from the inference result 204 and the ground truth data 205. As the loss function, an arbitrary function, for example, a square error or a cross entropy error can be used.

In step S204, the parameter updating unit 122 performs back propagation using the loss function calculated in step S203 as a starting point, and updates the parameter group of the convolutional neural network (CNN) 202 halfway through learning.

In step S205, the end determination unit 123 determines the end of the learning. To continue the learning (NO in step S205), the process returns to step S201 to similarly execute the processes of steps S201 to S204. When the processing is repeated while changing the input image 201 and the ground truth data 205, the parameters of the CNN 202 are repetitively updated such that the loss function lowers, and the accuracy of the machine learning apparatus 108 can be increased. If the learning is sufficiently done, and the end determination unit 123 determines to end the learning (YES in step S205), the processing is ended. The end of learning can be judged based on a judgement criterion set in accordance with a problem, for example, whether overlearning does not occur, and the accuracy of the inference result has a predetermined value or more, or whether the loss function has a predetermined value or less. Note that since the calculation cost of the processes of steps S201 to S205 is high, a calculation unit having high parallel calculation performance, such as a GPU, can also be used as the configuration of the learning unit 109.

Figure 3C:
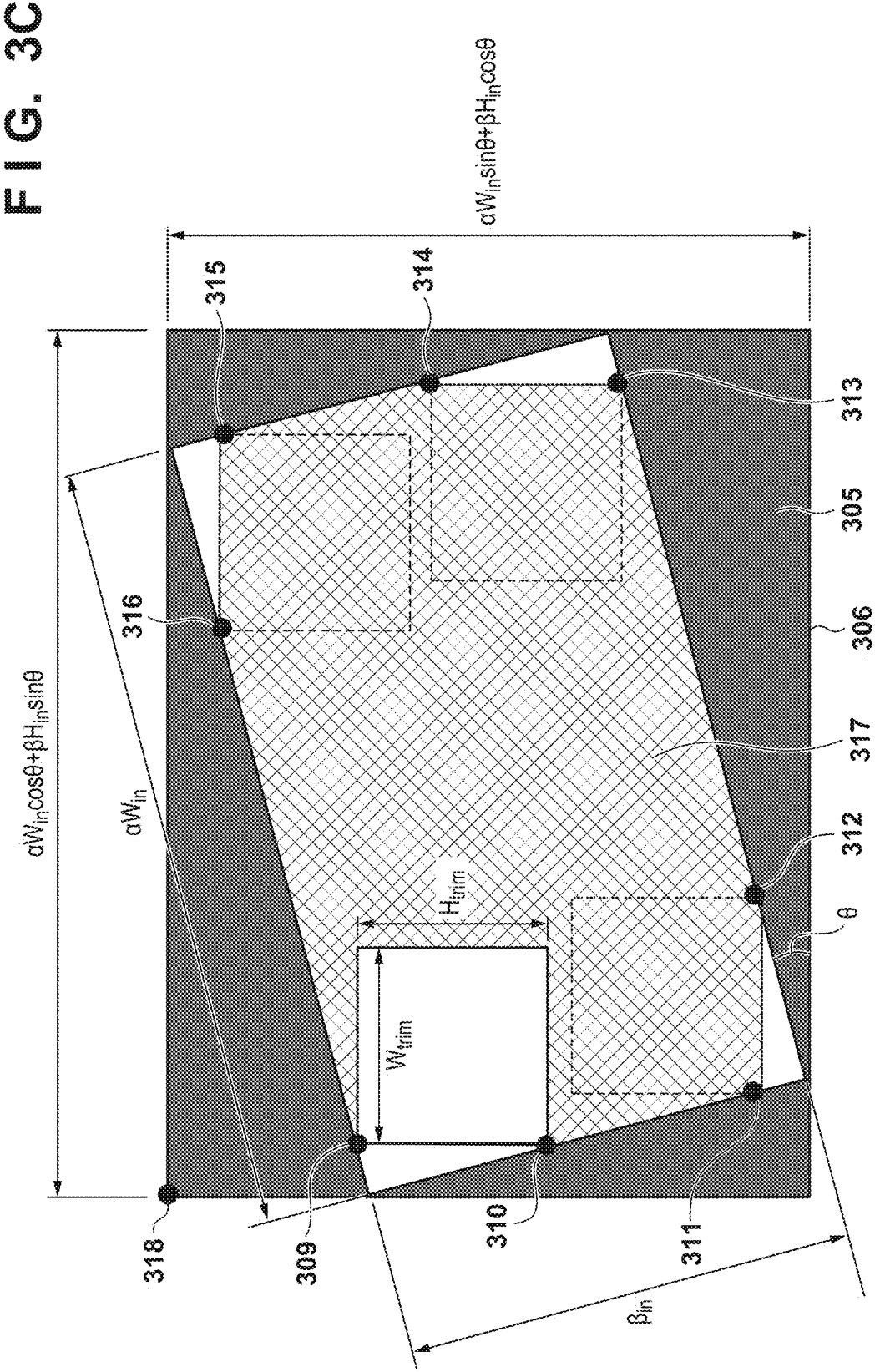
FIG. 3C is a view schematically showing an image example in data augmentation processing.

Processing of the data augmentation unit 120 will be described next with reference to FIGS. 3A, 3B, and 3C. FIG. 3A is a flowchart showing the procedure of processing of the data augmentation unit 120, and FIGS. 3B and 3C are views schematically showing image examples in data augmentation processing. At the time of learning when learning of the inference unit 121 is performed based on the training data, the data augmentation unit 120 performs data augmentation by increasing the number of input images that constitute the training data. The data augmentation unit 120 performs data augmentation such that a region where image information held by the input image is defective is not included.

The data augmentation unit 120 performs, for the training data, data augmentation using at least one augmentation processing of affine transform processing, extraction processing, and signal amount adjustment processing. The data augmentation unit 120 performs the same augmentation processing for the input image and the ground truth data. The data augmentation unit 120 augments training data by performing step S301 (affine transform processing), step S302 (extraction processing), and step S303 (signal amount adjustment processing). This can improve generalization performance in learning of the machine learning apparatus 108.

In step S301, the data augmentation unit 120 applies affine transform processing to training data, thereby rotating, inverting, enlarging, or reducing an image. The same affine transform is applied to, for example, the input image 201 and the ground truth data 205 shown in 2b of FIG. 2. An example of a labeling image having the same size as the input image 201 will be shown below as the ground truth data 205. Even if the ground truth data 205 is a labeling image whose size is different from the input image 201, or is an equation of a line or a curve representing the boundary of a desired region, augmentation processing having the same meaning as the data augmentation applied to the input image is performed for the ground truth data.

Let (x, y) be the coordinate system of the input image, (X', Y') be the coordinate system of a transformed image, and a, b, c, d, e, and f be the transform parameters of affine transform processing. In this case, affine transform processing can be expressed by equation (1) below. As the transform parameters $\underline{a}$ to f, arbitrary values can be selected for each training data. However, the range of values the transform parameters can take is limited by a rule to be described later.

$$\begin{pmatrix} x \\ y \end{pmatrix} = \begin{pmatrix} a & b \\ c & d \end{pmatrix} \begin{pmatrix} X' \\ Y' \end{pmatrix} + \begin{pmatrix} e \\ f \end{pmatrix} \qquad (1)$$

For example, to rotate the input image by θ and enlarge it to α times in the x-axis direction and β times in the y-axis direction, a=α cos θ, b=−α sin θ, c=β sin θ, d=β cos θ, and d=e=0 are set.

In step S302, the data augmentation unit 120 performs extraction processing for the transformed image, and outputs an extracted image. The data augmentation unit 120 selects the size (width and height) of the extracted image in accordance with the input/output size of the CNN 202.

Consider an example in which data augmentation is performed for an input image 301 including an object 302, a collimator region 303, and an irradiation field 304, as shown in B1 of FIG. 3B.

B2 of FIG. 3B is a view schematically showing an example of an image in a case in which the processes of steps S301 and S302 are applied to the original input image 301. Here, the data augmentation unit 120 affine-transforms the input image 301 in accordance with the processing of step S301, and generates a transformed image 306. After the transformed image 306 is generated, the data augmentation unit 120 performs extraction processing for the transformed image 306 in accordance with the processing of step S302, and generates an extracted image 307.

If rotation processing is included in affine transform, a defect region 305 including an invalid region where image information derived from the input image 301 is defective is generated in the transformed image 306.

Depending on the magnification factor in step S301 or the extraction position or the size of the extracted image in step S302, a part of the defect region 305 may be included in the extracted image 307, as shown in B2 of FIG. 3B.

The collimator region 303 is a region where radiation is shielded by an irradiation field stop and therefore exists to surround the outer periphery of the input image 301. As a characteristic feature, the image information (image signal) abruptly becomes small at the boundary to the irradiation field 304.

On the other hand, the defect region 305 is a region which exists to surround the outer periphery of the transformed image 306 and in which image information is defective, and has a characteristic feature close to the collimator region 303. However, although the collimator region 303 includes scattered rays derived from the object 302 and the irradiation field 304, the defect region 305 does not include the influence of such a physical phenomenon. For this reason, the defect region 305 has a similar but distinctly different characteristic feature from the collimator region 303. Note that since the signal of the collimator region 303 is generated by a complex physical phenomenon, it is difficult to artificially reproduce it in the defect region 305.

Irradiation field recognition processing is processing of classifying the collimator region 303 and the irradiation field 304. If the defect region 305 is included in the extracted image 307 to be used for learning because of data augmentation, the machine learning apparatus 108 learns information other than the feature of the collimator region 303, which should originally be learned, and the accuracy may lower due to data augmentation. Hence, to prevent the defect region 305 from being included in the extracted image 307, the transform parameters in the affine transform of step S301 and the position to extract the extracted image 307 in the extraction processing of step S302 need to be selected such that the defect region 305 is not included in the extracted image 307, as shown in B3 of FIG. 3B.

Limitation of the transform parameters for preventing the defect region 305 from being included in the extracted image 307 will be described next with reference to FIG. 3C.

As shown in FIG. 3C, consider an example in which the transform parameters in the affine transform of step S301 are set to a=α cos θ, b=−α sin θ, c=β sin θ, d=β cos θ, and d=e=0, and the input image 301 is enlarged by a magnification factor α in the x direction and by a magnification factor β in the y direction and rotated by a rotation angle θ. Letting Win be the image width of the input image 301, Hin be the height, $W_{trim}$ be the image width of the extracted image 307, and $H_{trim}$ be the height, the transformed image 306 having an image width of (αW$_{in}$ cos θ+βH$_{in}$ sin θ) and an image height of (αW$_{in}$ sin θ+βH$_{in}$ cos θ) and including the defect region 305 is generated by processing of the data augmentation unit 120.

In step S302, to prevent the defect region 305 from being included in the extracted image 307, the data augmentation unit 120 sets an extractable region 317 in the transformed image 306, and limits the range to acquire the extracted image 307.

The data augmentation unit 120 performs data augmentation by generating the extracted image 307 that extracts a part of the transformed image 306 obtained by affine transform of the input image constituting the training data, and limits the range to acquire the extracted image 307 such that the region (defect region 305) in which image information is defective is not included in the extracted image 307. The data augmentation unit 120 sets the extractable region 317 (FIG. 3C) in the transformed image 306, and limits the range to acquire the extracted image 307.

The data augmentation unit 120 can set the extractable region 317 in accordance with the rotation angle θ of the input image 301 in the affine transform. Also, the data augmentation unit 120 can set the parameters (magnification factors α and β) representing the magnification factors of the input image 301 in accordance with the rotation angle θ of the input image 301 in the affine transform. Here, the data augmentation unit 120 sets the rotation angle θ and the parameters (magnification factors α and β) representing the magnification factors of the input image 301 such that a part of the input image 301 is not made defective by the affine transform. The extracted image 307 is limited such that it is included in the extractable region 317 surrounded by vertices 309, 310, 311, 312, 313, 314, 315, and 316. When an origin 318 of coordinates is set at the upper left corner of the image, the coordinates (x, y) of the vertices x are given by the following equations. That is, the coordinates of the vertex 309 are given by equation (2), the coordinates of the vertex 310 are given by equation (3), the coordinates of the vertex 311 are given by equation (4), and the coordinates of the vertex 312 are given by equation (5). In addition, the coordinates of the vertex 313 are given by equation (6), the coordinates of the vertex 314 are given by equation (7), the coordinates of the vertex 315 are given by equation (8), and the coordinates of the vertex 316 are given by equation (9).

$$(x_{309}, y_{309}) = (H_{trim} \cos\theta \sin\theta, \alpha W_{in} \sin\theta - H_{trim} \sin^2\theta) \quad (2)$$

$$(x_{310}, y_{310}) = (H_{trim} \cos\theta \sin\theta, \alpha W_{in} \sin\theta + H_{trim} \cos^2\theta) \quad (3)$$

$$(x_{311}, y_{311}) = (\beta H_{in} \sin\theta - W_{trim} \sin^2\theta, \alpha W_{in} \sin\theta + \beta H_{in} \cos\theta - W_{trim} \cos\theta \sin\theta) \quad (4)$$

$$(x_{312}, y_{312}) = (\beta H_{in} \sin\theta + W_{trim} \cos^2\theta, \alpha W_{in} \sin\theta + \beta H_{in} \cos\theta - W_{trim} \cos\theta \sin\theta) \quad (5)$$

$$(x_{313}, y_{313}) = (\beta H_{in} \sin\theta + \alpha W_{in} \cos\theta - H_{trim} \cos\theta \sin\theta, \beta H_{in} \cos\theta + H_{trim} \sin^2\theta) \quad (6)$$

$$(x_{314}, y_{314}) = (\beta H_{in} \sin\theta + \alpha W_{in} \cos\theta - H_{trim} \cos\theta \sin\theta, \beta H_{in} \cos\theta - H_{trim} \cos^2\theta) \quad (7)$$

$$(x_{315}, y_{315}) = (\alpha W_{in} \cos\theta + W_{trim} \cos\theta \sin\theta, W_{trim} \cos\theta \sin\theta) \quad (8)$$

$$(x_{316}, y_{316}) = (\alpha W_{in} \cos\theta - W_{trim} \cos^2\theta, W_{trim} \cos\theta \sin\theta) \quad (9)$$

Here, concerning the image width W$_{in}$ of the input image, the image height H$_{in}$ of the input image, the magnification factors α and β, the rotation angle θ, and the image width W$_{trim}$ of the extracted image 307, and the image height H$_{trim}$ of the extracted image 307, the transform parameters can be set at random within the range that all the vertices 309 to 316 are included in the transformed image 306.

Note that when setting the transform parameters, if the magnification factors α and β are too large, or if the image width W$_{trim}$ of the extracted image 307 and the image height H$_{trim}$ of the extracted image 307 are much smaller than the image width $W_{in}$ of the input image and the image height $H_{in}$ of the input image, it is difficult to include the collimator region 303 in the extracted image 307, and it may be impossible to perform effective data augmentation. For this reason, the data augmentation unit 120 can set the magnification factors α and β to, for example, about 0.8 to 1.2 and set the transform parameters such that the length relationship between the image widths $W_{trim}$ and $H_{trim}$ of the extracted image 307 and $W_{in}$ and $H_{in}$ satisfies a ratio of, for example, about 1:2.

Considering that the rotation angle θ is, for example, 0° to 45°, the larger the rotation angle θ is, the larger the defect region 305 in the transformed image 306 is. Hence, when the magnification factors α and β are set large, the extracted range becomes wide. As described above, the magnification factors α and β of the transform parameters may be changed in synchronism with the size of the defect region 305 generated by the rotation angle θ.

In step S303, the data augmentation unit 120 performs signal amount adjustment processing for the extracted image 307, and outputs an adjusted image. As the signal amount adjustment processing, the data augmentation unit 120 performs, for the extracted image 307, multiplication using an arbitrary coefficient and addition using an arbitrary coefficient. In the signal amount adjustment processing, letting $I_{trim}$ be the extracted image 307, and $I_{out}$ be the adjusted image, and assuming that coefficients γ and δ are arbitrary coefficients, the relationship between the extracted image 307 ($I_{trim}$) and the adjusted image ($I_{in}$) can be represented by $$I_{out} = \gamma I_{trim} + \delta \qquad (10)$$

Here, as the coefficient γ, an arbitrary coefficient of about 0.1 to 10 may be set, and the extracted image $I_{trim}$ may be multiplied by that to uniformly increase/decrease the signal. Alternatively, a two-dimensional filter such as a Gaussian filter may be set and applied to the extracted image $I_{trim}$. As for the coefficient δ as well, a uniform value may be added/subtracted, or arbitrary random noise may be added for each pixel. When adding noise, noise according to the physical characteristic of the radiation detection apparatus 104 can also be added.

Note that the flowchart of FIG. 3A shows an example in which steps S301 to S303 are sequentially processed. However, the steps need not be performed in this order. Only some of the processes may be performed, or the order of the processes may arbitrarily be changed. In addition, another arbitrary data augmentation method may be used as long as a region where image information is defective is not newly generated by data augmentation.

For example, if affine transform processing of step S301 is not performed, to prevent the defect region 305 from being included in the extracted image 307, the data augmentation unit 120 can set the extractable region 317 in the input image to limit the range to acquire the extracted image 307.

That is, the data augmentation unit 120 performs data augmentation by generating the extracted image 307 that extracts a part of the input image 301 constituting training data, and limits the range to acquire the extracted image 307 such that the region (defect region 305) where image information is defective is not included in the extracted image 307. The data augmentation unit 120 sets the extractable region 317 (FIG. 3C) in the input image 301, and limits the range to acquire the extracted image 307.

As for the processing of the inference unit 110 in the machine learning apparatus 108, a case in which a convolutional neural network (CNN) is used will be described next as an example with reference to FIG. 4. FIG. 4 is a view schematically showing the concept of inference of the inference unit 110.

The inference unit 110 is an inference unit learned by the learning unit 109, and can perform inference processing based on learned parameters acquired based on learning. The inference unit 110 includes a learned convolutional neural network (CNN) 402 having a learned parameter group obtained by the learning unit 109. The inference unit 110 applies inference processing by the learned CNN 402 to an input image 401 input to the inference unit 110, and outputs an inference result 403.

Note that for learning in the machine learning apparatus 108, for example, it is preferable that learning is performed before introduction to the use environment of the user, and the parameter group of the learned CNN 402 is obtained in advance. However, it is also possible to update the machine learning apparatus 108 in accordance with a use situation after introduction to the use environment of the user. In this case, a set of an image acquired in the use environment of the user and the data set of an irradiation field is stored as training data in the storage device 115.

Using the set of the data set stored in the storage device 115 as new training data, the learning unit 109 of the machine learning apparatus 108 can perform additional learning and update the parameter group of the learned CNN 402. In the use environment of the user, the additionally learned inference unit 110 can perform inference processing based on the result of learning to which a set of an image captured using the radiation imaging system 100 and the data of an irradiation field corresponding to the image is added as training data, and the result of learning performed in advance.

As for the timing of performing additional learning, the learning unit 109 can select the timing of executing additional learning from, for example, the timing when a predetermined number or more of data sets are accumulated in the storage device 115, the timing when a predetermined number or more of data sets in which the irradiation field recognition processing results are corrected by the user are accumulated, and the like. In addition, as the initial value of the parameter group of the CNN when additionally performing learning, the parameter group of the learned CNN 402 used before the additional learning may be set to perform transfer learning.

Note that the storage device 115 and the machine learning apparatus 108 need not always be mounted on the information processing apparatus 107, and the storage device 115 and the machine learning apparatus 108 may be provided on a cloud server connected via a network. In this case, data sets obtained by a plurality of radiation imaging systems 100 may be collected/stored on the cloud server, and the machine learning apparatus 108 may perform additional learning using the data set collected/stored on the cloud server.

As described above, according to this embodiment, it is possible to provide a machine learning technique capable of more accurately extracting a region by performing appropriate data augmentation for training data used in learning.

According to the present invention, it is possible to provide a machine learning technique capable of more accurately extracting a region by performing appropriate data augmentation for training data used in learning.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A machine learning apparatus for extracting a region from an input image, comprising:
    at least one of (a) one or more processors connected to one or more memories storing a program including instructions executed by the one or more processors and (b) circuitry configured to function as:
        an inference unit configured to output the region by inference processing for the input image; and
        an augmentation unit configured to, in learning when learning of the inference unit is performed based on training data that is constituted by a set of the input image and ground truth data corresponding to the input image and representing an extraction region, perform data augmentation by increasing the number of input images constituting the training data,
        wherein the augmentation unit performs the data augmentation such that a region where image information held by the input image is defective is not included.

2. The machine learning apparatus according to claim 1, wherein
    the augmentation unit performs the data augmentation for the training data by at least one augmentation processing of affine transform processing, extraction processing, and signal amount adjustment processing, and
    the augmentation unit performs the same augmentation processing for the input image and the ground truth data.

3. The machine learning apparatus according to claim 2, wherein
    the augmentation unit performs the data augmentation by generating an extracted image that extracts a part of the input image constituting the training data, and
    a range to acquire the extracted image is limited such that the region where the image information is defective is not included in the extracted image.

4. The machine learning apparatus according to claim 3, wherein the augmentation unit sets an extractable region in the input image and limits the range to acquire the extracted image.

5. The machine learning apparatus according to claim 3, wherein as the signal amount adjustment processing, the augmentation unit performs, for the extracted image, multiplication using an arbitrary coefficient and addition using an arbitrary coefficient.

6. The machine learning apparatus according to claim 2, wherein
    the augmentation unit performs the data augmentation by generating an extracted image that extracts a part of a transformed image obtained by affine transform of the input image constituting the training data, and
    a range to acquire the extracted image is limited such that the region where the image information is defective is not included in the extracted image.

7. The machine learning apparatus according to claim 6, wherein the augmentation unit sets an extractable region in the transformed image and limits the range to acquire the extracted image.

8. The machine learning apparatus according to claim 7, wherein the augmentation unit sets the extractable region in accordance with a rotation angle of the input image in the affine transform.

9. The machine learning apparatus according to claim 6, wherein the augmentation unit sets a parameter representing a magnification factor of the input image in accordance with the rotation angle of the input image in the affine transform.

10. The machine learning apparatus according to claim 9, wherein the augmentation unit sets the rotation angle and the parameter representing the magnification factor of the input image such that a part of the input image is not made defective by the affine transform.

11. The machine learning apparatus according to claim 1, wherein the ground truth data is a labeling image formed by labeling the extraction region in the input image using an arbitrary value.

12. The machine learning apparatus according to claim 1, wherein the ground truth data is coordinate data representing the extraction region in the input image by coordinates.

13. The machine learning apparatus according to claim 1, wherein the ground truth data is data that specifies a boundary of the extraction region in the input image by a line or a curve.

14. The machine learning apparatus according to claim 1, wherein the inference unit performs the inference processing based on a learned parameter acquired based on the learning.

15. The machine learning apparatus according to claim 1, wherein the machine learning apparatus extracts the region from the input image based on supervised learning using a convolutional neural network.

16. The machine learning apparatus according to claim 1, wherein the input image is an image captured using a radiation imaging system, and
    the region is an irradiation field irradiated with radiation by the radiation imaging system.

17. The machine learning apparatus according to claim 16, wherein in a use environment of a user, the inference unit performs the inference processing based on a result of learning to which a set of the image captured using the radiation imaging system and data of the irradiation field corresponding to the image is added as training data, and a result of learning performed in advance.

18. A radiation imaging system comprising:
the machine learning apparatus according to claim 1; and
a radiation detection apparatus that detects radiation, wherein the radiation detection apparatus are communicatively connected to the machine learning apparatus.

19. A machine learning method by a machine learning apparatus including inference unit configured to output a region by inference processing for an input image and configured to extract the region from the input image, comprising
performing, in learning when learning of the inference unit is performed based on training data that is constituted by a set of the input image and ground truth data corresponding to the input image and representing an extraction region, data augmentation by increasing the number of input images constituting the training data,
wherein the data augmentation is performed such that a region where image information held by the input image is defective is not included.

20. A non-transitory computer-readable storage medium storing a program for causing a computer to execute the machine learning method according to claim 19.

21. A machine learning apparatus for extracting a region that is an irradiation field irradiated with radiation by a radiation imaging system from an input image that is an image captured using the radiation imaging system, the machine learning apparatus comprising:
at least one of (a) one or more processors connected to one or more memories storing a program including instructions executed by the one or more processors and (b) circuitry configured to function as:
an inference unit configured to output the region by inference processing for the input image; and
an augmentation unit configured to, in learning when learning of the inference unit is performed based on training data, perform data augmentation by increasing the number of input images constituting the training data,
wherein the augmentation unit performs the data augmentation such that a region where image information held by the input image is defective is not included.

22. A radiation imaging system comprising:
the machine learning apparatus according to claim 21; and
a radiation detection apparatus that detects radiation, wherein the radiation detection apparatus are communicatively connected to the machine learning apparatus.

23. A machine learning method by a machine learning apparatus including inference unit configured to output a region that is an irradiation field irradiated with radiation by the radiation imaging system by inference processing for an input image that is an image captured using a radiation imaging system and configured to extract the region from the input image, comprising
performing, in learning when learning of the inference unit is performed based on training data that is constituted by a set of the input image and ground truth data corresponding to the input image and representing an extraction region, data augmentation by increasing the number of input images constituting the training data,
wherein the data augmentation is performed such that a region where image information held by the input image is defective is not included.

24. A non-transitory computer-readable storage medium storing a program for causing a computer to execute the machine learning method according to claim 23.

25. An information processing apparatus comprising:
at least one of (a) one or more processors connected to one or more memories storing a program including instructions executed by the one or more processors and (b) circuitry configured to function as:
an inference unit configured to perform inference processing on a input image using parameter obtained by learning using a training data that is constituted by input images and ground truth data corresponding to the input image, wherein the input images are obtained by augmentation process by extracting a part of an image obtained by a transform process including rotation process.

26. The information processing apparatus according to claim 25, wherein the inference unit outputs a region that is an irradiation field irradiated with radiation by performing the inference processing.

27. A radiation imaging system comprising:
the information processing apparatus according to claim 25; and
a radiation detection apparatus that detects radiation, wherein the radiation detection apparatus are communicatively connected to the information processing apparatus.

28. An information processing method comprising:
performing inference processing on an input image using parameter obtained by learning using a training data that is constituted by input images and ground truth data corresponding to the input image, wherein the input images are obtained by augmentation process by extracting a part of an image obtained by a transform process including rotation process.

29. A non-transitory computer-readable storage medium storing a program for causing a computer to execute the information processing method according to claim 28.

* * * * *